United States Patent [19]
Marchant et al.

[11] Patent Number: 5,993,890
[45] Date of Patent: *Nov. 30, 1999

[54] NONTHROMBOGENIC IMPLANT SURFACES

[75] Inventors: Roger E. Marchant, Cleveland Heights; Shengmei Yuan, Cleveland; Gyongyi Szakalas-Gratzl, Chagrin Falls, all of Ohio

[73] Assignee: Case Western Reserve University, Cleveland, Ohio

[ * ] Notice: This patent is subject to a terminal disclaimer.

[21] Appl. No.: 08/911,786

[22] Filed: Aug. 15, 1997

Related U.S. Application Data

[63] Continuation of application No. 08/254,492, Jun. 6, 1994, Pat. No. 5,741,852, which is a continuation of application No. 07/979,157, Nov. 19, 1992, abandoned.

[51] Int. Cl.$^6$ .................................................. C08G 81/00
[52] U.S. Cl. .......................... 427/2.3; 428/409; 428/543; 523/105; 523/112; 525/54.3; 525/937; 527/300; 527/312
[58] Field of Search ............................... 525/54.2, 54.3, 525/937; 527/300, 312; 427/2.3; 428/409, 543; 523/105, 112

[56] References Cited

U.S. PATENT DOCUMENTS

| | | |
|---|---|---|
| 4,518,701 | 5/1985 | Khanna et al. . |
| 5,198,493 | 3/1993 | Holmberg et al. . |
| 5,217,492 | 6/1993 | Guire et al. . |
| 5,741,852 | 4/1998 | Marchant et al. ............... 525/54.3 |

OTHER PUBLICATIONS

M.V. Sefton, et al., "Preparation of Nonthrombogenic Materials by Chemicals by Chemical Modification" *Blood Compatibility*, vol. 1, pp. 151–198 (book, no month).

M. Yalpani, et al., "Selective Chemical Modifications of Dextran", *J. Polymer Sci. Poly. Chem. Ed.,* 23, 1395–1405 (May 1985).

K. Hashimoto, et al. "Chemical Modification of the Reducing Chain End in Dextrans and Trimethylsilation of its Hydroxyl Groups", *J. Poly. Sci. Polym. Chem. Ed.,* 29, 1271–1279 (Aug. 1991).

K. Hashimoto, et al., "Synthesis of Block Copolymer Containing Dextran and Polyamide Sequences" *J. Polym. Sci. Polym. Chem. Ed.,* 30, 211–220 (Feb. 1992).

W.W. Emmerling, et al. "Chemical Synthesis of Branched Polysaccharides Binding Mono–Di–and Oligosaccharides to Various Carriers via Amide Linkage" *Makromol. Chem.,* 179, 1627–1633 (Jun. 1978).

K. Kurita, et al. "Studies on Chitin 13 New Polysaccharide/Polypeptide Hybrid Materials On Chitin and Poly(methyl L–glutemate)", *Macromolecules,* 21, 1579–1588 (Jun. 1988).

M. Mora, et al., "Polymeric Prodrugs, Synthesis and Hydrolytic Behavior of Dextran–Bound Anticancer Agents", *Makromol. Chem.,* 191, 1051–1056 (May 1990).

K. Kobayashi, et al., "Synthesis and Functions of Polystyrene Derivatives Having Pendant Oligosaccharide" *Polymer J.,* 17, 567–575 (Apr. 1985).

G. Johansson, et al., "Affinity Partitioning of Phosphofructokinase From Baker's Yeast Using Polymer–Bound Cibacron Blue F3G–A", *Eur. J. Biochem.,* 131, 589 (Apr. 1983).

S.W. Tay, et al., "Activity Toward Thrombin–Antithrombin of Heparin Immobilized on Two Hydrogels" *Biomaterials,* 10, 11–15 (Jan. 1989).

Kodama, et al., "Antithrombin III Binding to Surface Immobilized Heparin and its Relation to Factor XA Inhibition", *Thrombosis and Haemostasis,* 58, 1064–1067 (Dec. 1987).

Grainger, et al, "Poly(dimethylisiloxane)–poly(ethylene oxide)–heparin Block Copolymers. I. Synthesis and Characteristics", *J. Biomed. Mater. Res.* 22, 231–249 (Mar. 1988).

Hoffman, et al., "A New Method for Covalently Coupling Primary Amino Groups", *Carbohydrate Research,* 117, 328–331 (Jun. 1983).

Vulvic, et al., "Improved Synthesis of Polystyrene–Poly-(ethylene oxide)–Heparin Block Copolymer",*J. Polym. Sci., Part A:, Polym. Chem.,* 28, 1693–1720 (Jun. 1990).

Grode, et al. "Nonthrombogenic Materials via a Single Coating Process", *Trans. Am. Soc. Artif. Intern. Organs,* 15, 1 (Apr. 1969).

Park et al. "Heparin Immobilization Onto Segmented Polyurethane urea Surfaces—Effect of Hydrophilic Spacers", *J. Biomed. Mater. Res.,* 22, 977 (Nov. 1988).

Lee, et al. "Protein–Resistant Surfaces Prepared by PEO Containing Block Copolymer Surfactants" *J. Biomed. Mater. Res.,* 23, 351–368 (Mar. 1989).

Lee, et al. "Surface Properties of Copolymers of Alkyl Methacrylates with Methoxy Polyethylene Oxide Methacrylates and Their Application as Protein Resistant Coating", *Biomaterials,* 11, 455–464 (Sep. 1990).

Jeon, et al. "Protein–Surface Interactions in the Presence of Polyethylene Oxide –I. Simplified Theory" *J. Coll. Interface Sci.* 142, 149–158 (Mar. 1991).

Kim, et al. "A New Class of Biodegradable Polymers" *J. Polym. Sci. Poly. Lett. Ed.* 11,731 (Dec. 1973).

Lynn, et al. "Synthesis and Biodegradability of Amylose Block Copolymer" *J. Polym. Sci. Polym. Chem. Ed.,* 18, 1967 (Jun. 1980).

Lee, et al. "Amylose–Polyester Block Copolymers" *J. Polym. Sci. Polym. Chem. Ed.* 20 997 (Apr. 1982).

(List continued on next page.)

*Primary Examiner*—Jeffrey C. Mullis
*Attorney, Agent, or Firm*—Calfee, Halter & Griswold LLP

[57] ABSTRACT

Triblock polymers comprised of polysaccharide, such as heparin or dextran, and a hydrocarbon chain, have been prepared. The triblock polymer adsorbs strongly on the surface of hydrophobic polymer substrates such as polyethylene, through hydrophobic interaction between the polymer and the hydrophobic hydrocarbon chain of the triblock polymer. The surface adsorbed with triblock polymer is resistant to protein deposition, which renders the surface nonthrombogenic.

31 Claims, 8 Drawing Sheets

OTHER PUBLICATIONS

T. Mezger, et al. "Cellulose Containing Block Copolymers", *Die. Angewandte Makromolekulare Chemie,* 116, 13–27 (Sep. 1983).

Mezger, et al. "Cellulose Containing Block Copolymers 5a) Three–Block Copolymer Synthese Via Macroinitiator" *Makromol. Chem. Rapid. Commun.*, 313–320 (May 1983).

Miyamoto et al. "Preparation of Cellulose Graft Copolymers Having Polypeptide Side Chains and Their Blood Compatibility", *J. Appl. Polym. Sci.* 31 2303–2314 (May 1986).

Pfannemuller et al. "Lineare and Sternformige Hybride–Polymer 4a) Ein Neuer Weg Zur Synthese Von Cellulose Und Amylose Enthaltenden Blockcopolymer" *Makromol. Chem.* 189, 19654–1985 (Sep. 1988).

Kobayashi, et al. "Grafting of 2–oxazolines onto cellulose and cellulose diacetate", *Makromolecules,* 21, 1921–1925, (Jul. 1988).

Okada, et al. "Polymerization of Bicyclic Acetals, 14a) Synthesis of an amphiphilic block copolymer via Ring–opening polymerization of 6,8–dixoabicyclo[3.2.1] octane with a polysaccharide macroinitiator" *Makromol. Chem.* 189, 263 (Feb. 1988).

Kumar, et al. "Biodegradable Polymers: Prospects, Problems, and Progress" *J. Macromol. Sci. Rev.,* C22 (2), 225–260 (1982-3).

Bamford, et al. "Chemical Modification of Polymers Intended to Increase Blood Compatibility", *Bull. Soc. Chim. Belg.,* vol. 99, 919n 11–12, 1990.

Feger, et al. "Cellulose Containing Block Copolymers" *Polymer Bulletin,* Nov. 7, 1980, pp. 407–413.

Marchant, et al. "Interactions of plasma proteins with a novel polysaccharide surfactant physisorbed to polyethylene" *J. Biomater. Sci. Polymer. Edn.,* vol. 6, pp. 549–564 (1994).

Zhang, et al. "Novel Polysaccharide Surfactants: Synthesis of Model Compounds and Dextran–Based Surfactants", *Macromolecules,* 1994, 27.

Zhang, et al. "Novel Polysaccharide Surfactants: The Effect of Hydrophobic and Hydrophilic Chain Length on Surface Active Properties", *J.Coll. and Interface Sci.,* 177, (1996).

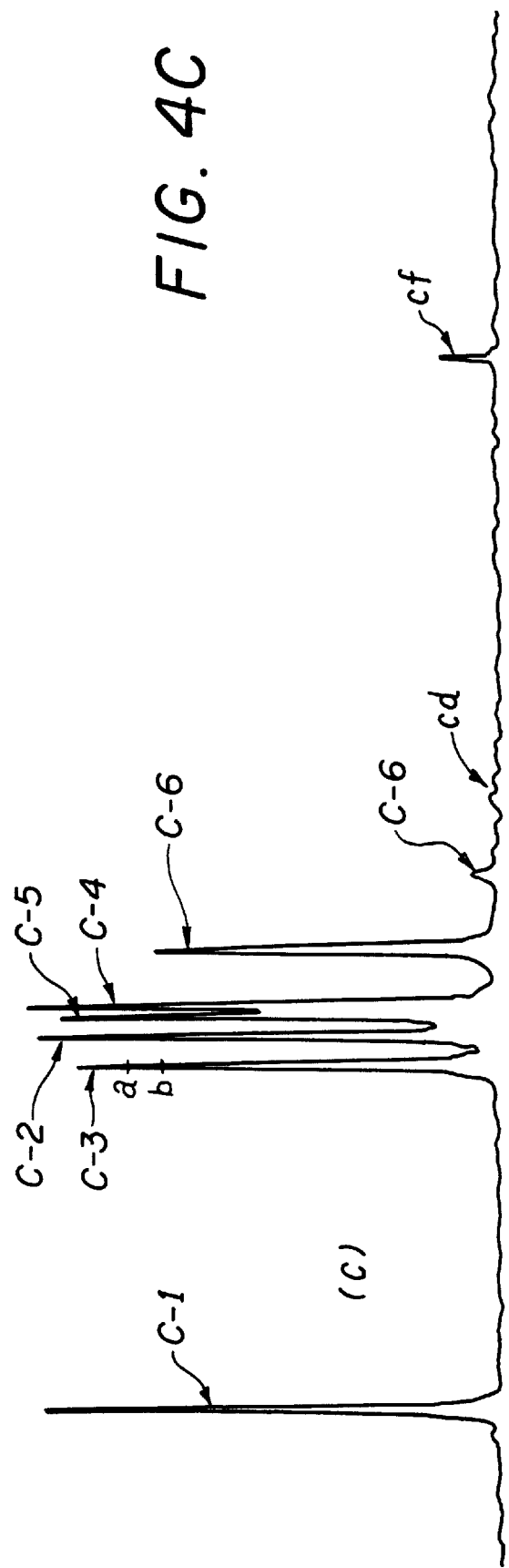

MDPEPLASD  PTFEMD35A
PTFEA

NONTHROMBOGENIC IMPLANT SURFACES

CROSS-REFERENCE TO RELATED APPLICATIONS

This application is a continuation of U.S. patent application Ser. No. 08/254,492, filed Jun. 6, 1994, which issued as U.S. Pat. No. 5,741,852 on Apr. 21, 1998, and which was a continuation of U.S. patent application Ser. No. 7/979,157, filed Nov. 19, 1992, now abandoned.

BACKGROUND OF THE INVENTION

The use of synthetic biomaterials to sustain, augment or completely replace diseased human organs has increased tremendously over the past thirty years. Synthetic implants have cardiovascular applications such as vascular grafts, heart valves, and ventricular assist devices; extracorporeal systems; and a wide range of invasive treatment and diagnostic systems. Unfortunately, existing biomaterials suffer from well-known problems associated with surface-induced thrombosis or clot formation such as thrombotic occlusion and thromboemboli, and infection. Synthetic vascular grafts having a diameter less than 6 mm are currently impracticable, because of potential thrombotic occlusion, and the artificial heart has been plagued with problems of thromboemboli and infection. Advances in the development of artificial organs and artificial vascular grafts have resulted in the need for nonthrombogenic materials.

Thrombosis is initiated by the deposition of a plasma protein layer on the surface of the implanted biomaterial. Thereafter, platelets, fibrin, and possibly leukocytes, adhere to the deposited protein. The interactions between the plasma proteins and the surface of the implant determine the adhesion, the activation and the spreading of platelets, the activation of coagulation, cell attachment and protein deposition. However, at the molecular level, the fundamental forces and interactions of plasma proteins with implants is not well understood.

There have been several attempts to create nonthrombogenic surfaces on polymer implants thereby increasing the blood-biocompatibility of implants.

Early attempts included precoating the implants with proteins not involved in thrombosis, such as albumin, to mask the thrombogenic surface of the implant. However, such implants loose their nonthrombogenic properties within a short time. Attempts have been made to mask the thrombogenic surface by coating gelatin onto implants such as ventricular assist devices. While the gelatin coating reduced the thrombus formation, it did not adhere to the implant and it did not prevent thromboemboli and infection.

Attempts have been made to render implants nonthrombogenic by coating the surface of the implant with polyethylene oxide to mask the thrombogenic surface of the implant; it was discovered that such a coating at times also reduced protein adsorption. While this reduced thrombogenesis, the coupling of polyethylene oxide to the surface of the implant involves very complex procedures, and the coated implants do not consistently exhibit protein resistance.

There have been many attempts to prepare nonthrombogenic surfaces by attaching heparin to biomaterials, because of heparin's potent anticoagulant properties. However, each method requires that the implant surface be first modified by attachment of a coupling molecule before heparin can be attached. For example, the positively charged coupling agent tridodecylmethylammonium chloride, is coated onto an implant, which provides a positively charged surface and allows heparin which has a high negative charge density, to be attached. However, the heparin slowly dissociates from the surface, to expose the positively charged, TDMAC surface which is particularly thrombogenic. The TDMAC attracts platelets and other cells; cells surfaces have a high negative charge density. Thus the TDMAC heparin coated implant is successful only for short term implants such as catheters.

Implants coated with heparin coupled to coupling molecules typically have limited anti-thrombogenic effectiveness because commercial heparin preparations contain the protein core and because many heparin molecules which having no anticoagulant activity. As a result, the surfaces soon become covered by adsorbing protein on exposure to blood, thus neutralizing the anticoagulant activity of the active heparin molecule.

It is desirable to have implants which resist plasma protein deposition, and to have a simple procedure for modifying the surface of implants. Nonthrombogenic implants would reduce the need for aggressive anticoagulant therapy, improve the performance of implants, particularly cardiovascular prosthetic devices, and encourage the development of devices not currently feasible.

SUMMARY OF THE INVENTION

The present invention provides a triblock polymer which may be easily applied to the surface of a hydrophobic substrate, such as an implant, to provide the substrate with resistance to the deposition of plasma proteins thereby preventing the first step of thrombus formulation. The triblock polymer contains two hydrophilic segments which are joined via a hydrophobic segment. The hydrophobic segment is a hydrocarbon chain which hydrophobically interacts with the surface of the hydrophobic substrate to provide a means of attaching the triblock polymer to the surface of the substrate. The hydrophilic segments are oligosaccharides or polysaccharides, such as, for example dextran, dextran sulfate, dermatan sulfate, heparin or portions of heparin. The hydrophobic substrates include biomaterials that are hydrophobic, for example, polyethylene, polypropylene, silicone rubber, Impra®, Gortex® and Teflon®, and hydrophobic medical polyurethanes such as Pellethanes®.

The triblock polymer is easily applied to the substrate. Since the free triblock polymer is water soluble, the triblock polymer is dissolved in water and the implant is then immersed in the aqueous solution of the triblock polymer for about 24 hours. The triblock polymer spontaneously attaches to the polymeric substrate to provide a protein-resistant, nonthrombogenic surface.

BRIEF DESCRIPTION OF THE DRAWINGS

FIG. 4C is the $^{13}$C-NMR spectra of the dextran triblock polymer.

DETAILED DESCRIPTION OF THE INVENTION

Figure 1:
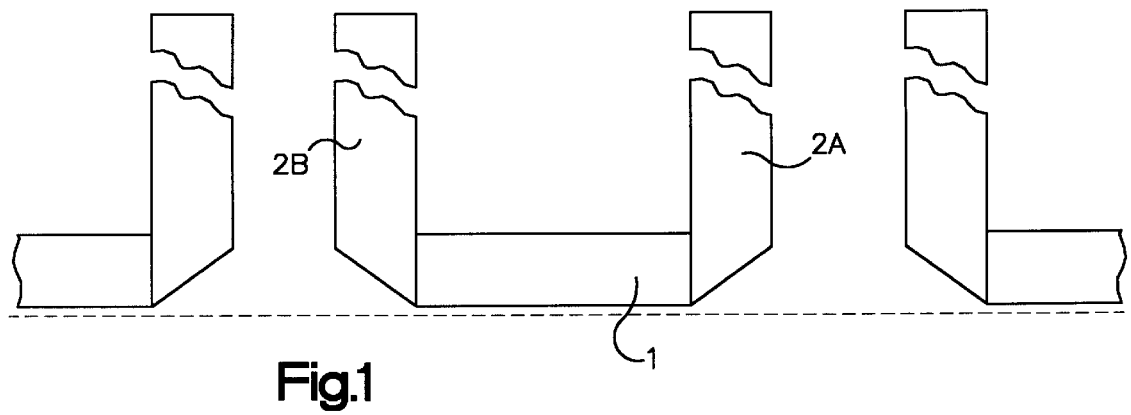
FIG. 1 is a representation of triblock polymer on a substrate.

The present invention provides a triblock polymer which contains two hydrophilic blocks or segments, bridged by a hydrophobic block or segment, as shown in FIG. 1. The hydrophobic block 1 is a hydrocarbon chain that attaches spontaneously and irreversibly to the hydrophobic substrates through hydrophobic interactions to provide a means of attaching the triblock polymer to the surface of the substrate. The hydrophilic segments 2A and 2B are polysaccharides or oligosaccharides, such as, for example, dextran, dextran sulfate, dermatan sulfate or polysaccharides or oligosaccharides of heparin. Hereinafter the term "polysaccharide" includes oligosaccharide. The triblock polymer adsorbs strongly on the surface of hydrophobic substrates, such as for example, polyethylene, polypropylene, silicon rubber, Impra®, Gortex®, Teflon®, and hydrophobic medical polyurethanes such as Pellethanes®.

The free triblock polymer is water soluble; the triblock polymer is dissolved in water and the implant is then immersed in the aqueous solution of the triblock polymer for about 24 hours. The triblock polymer spontaneously attaches to the substrate to provide a nonthrombogenic surface.

Protein adsorption from blood plasma is governed by the surface properties of the plasma proteins and the substrate, and by the process of mass transport in the near-surface layer, which is determined by the hydrodynamic conditions. The three dimensional structure of a protein, and hence its surface, is stabilized, at about 5–15 kcal/mol by intramolecular and intermolecular forces, including attractive van der Waals forces, and strong hydrophobic interactions that result from the attraction between nonpolar species in an aqueous medium. Common biomaterials are all hydrophobic so that attractive interfacial hydrophobic interactions with protein molecules results in a strong entropic driving force for the adsorption, of plasma proteins particularly with any hydrophobic domains on the protein. Albumin, in particular, strongly interacts with hydrophobic surfaces; and high albumin adsorption often occurs on implants. Similarly, proteins present in low concentration in plasma will adsorb in relatively high amounts, if strong attractive forces are present between the substrate and the protein. Hydrophobic interactions and binding diminishes with increasing polar character of the polymer substrate, and, depending on the prevailing interfacial force, this may lead to reduced adsorption or to an adsorbed protein layer of different composition. For example, fibronectin adsorption increases as the hydrophilicity of the substrate is increased.

For highly hydrated biomaterials, such as a substrate having immobilized polyethylene oxide (PEO), entropic repulsive forces (ERF), also referred to as repulsive hydration forces, or steric repulsion, are important in resisting protein deposition. ERF is the long range (0–150 nm) repulsive force that arises from the dynamic motions and segmental interactions of hydrated macromolecular chains. The strength of the repulsive force increases as the size and mobility of the hydrated chain is increased. However, chain length, configurational flexibility, surface chain density, and substrate topography and heterogeneity of the macromolecule are all believed to affect the adsorption and strength of the repulsive force. For many macromolecules such as heparin, which have a high charge density, the complex three-dimensional charge distribution constitutes either an additional electrostatic repulsive force, or a recognition sequence, such as the pentasaccharide antithrombin binding sequence in heparin, which provides an attractive force sufficient to overcome ERF at short distances. This has permitted the biological macromolecules in blood to achieve highly evolved functional specificity. Interfacial forces are important in both polysaccharide-protein and polysaccharide-cell repulsive and attractive interactions.

It is believed the surface attachment of the triblock polymers of the present invention involves a long range interfacial force. The ERF results from the presence of highly hydrated polymer chains extending out from the surface of the substrate. The ERF increases with a high radius of gyration, that is, chain length, for the hydrated polysaccharide and with high surface density on the substrate. The triblock polymer structure is designed to maximize the interfacial effects of repulsive forces to increase resistance to protein adsorption and attractive forces to promote attachment of the triblock polymer. The dextran-hydrocarbon-dextran triblock polymer (hereinafter "dextran triblock polymer") provides hydrophobic substrates with a highly hydrated, neutral, biological molecule at the surface, which maximize ERF. The dextran sulfate-hydrocarbon-dextran sulfate triblock polymer provides a highly hydrated, negatively charged molecule at the substrate surface that maximizes the ERF with repulsive electrostatic force. Similarly, heparin-hydrocarbon-heparin triblock polymers in which the heparin polysaccharides have very low affinity for antithrombin III, (ATIII), involve ERF with repulsive electrostatic force. The heparin-hydrocarbon-heparin triblock polymer in which the heparin polysaccharides have high affinity ("HA") for ATIII involves ERF with repulsive electrostatic force. The HA heparin has specific anticoagulant activity achieved through strong specific electrostatic attractive force between antithrombin and a unique pentasaccharide binding sequence present in the HA heparin.

The Polysaccharide

The hydrophilic portion of the triblock polymer is a polysaccharide preferably having an average molecular weight of from about 4,000 to about 500,000, more preferably about 6,000 to about 150,000. The polysaccharide can be a polymer of glucose, such as, for example, dextran or the polysaccharide portion of the glycoprotein, heparin. Good results have been obtained using dextran having a average molecular weight of about 8,800 available from Sigma Chemical Company and with polysaccharides of heparin in the molecular weight range 5,000 to 20,000.

The dextran polysaccharide is a neutral hydrated molecule so that plasma proteins are repelled by ERF. The heparin polysaccharides are hydrated and negatively charged which provides an additional electrostatic repulsive force that further repels plasma proteins and cellular elements such as platelets.

Some of the individual heparin polysaccharide molecules of the mixed affinity heparin, contain the unique pentasaccharide sequence that is essential for heparin's anticoagulant activity. The heparin product of deaminative cleavage possesses a terminal 2,5 anhydromanose unit. The terminal aldehyde of the 2,5 anhydromanose binds to one of the terminal diamines on the hydrocarbon chain via reductive amination. Thus a heparin triblock polymer is prepared which contains a mixture of heparin polysaccharides having various affinities for ATIII.

Other suitable polysaccharide include the dermatan sulfate, and dextran sulfate, which are hydrated and negatively charged and serves to repulse proteins and platelets.

The Hydrocarbon Chain

The hydrophobic segment of the triblock polymer is a hydrocarbon chain of sufficient length, at least 5 carbons, so as to provide a sufficient area for hydrophobic interaction between the substrate and the triblock polymer thereby serving to bind to triblock polymer to the substrate. The upper limit of the number of carbons in the hydrocarbon chain number is determining by the number of carbons that renders the triblock polymer insoluble in the aqueous medium. The solubility of the triblock polymer depends upon the type and molecular weight of the polysaccharide selected for the triblock polymer. Preferably the hydrocarbon chain has from 5 to 18 carbons, more preferably from 6–12 carbons. The selection of the hydrocarbon chain depends upon the polysaccharide of the triblock polymer. It is believed that the more hydrophilic the polysaccharide, the more it will tend to interact with the surrounding plasma and the more the triblock will tend to be pulled from the substrate. In such a case the length of the hydrocarbon chain is increased to provide a greater surface area for interaction with the substrate. However, hydrocarbon chains having less than 19 carbons are generally preferred since their smaller size permits a greater number of triblock polymer molecules to bind to the substrate. It is believed that the greater the density of triblock polymer bound to the substrate, the greater the resistance to protein deposition. Good results have been obtained using 1,6-hexanediamine and 1,12-diamineododecane as the hydrocarbon chain.

The Substrate

Any substrate with sufficient hydrophobicity to bind the hydrocarbon chain is a suitable substrate for the triblock polymer; however, for biological implants, the substrate material must also be biocompatible. Such biocompatible materials are known in the art, and include for example, polyethylene available from Abiomed Inc. in Danvers, Mass. and poly tetrafluoroethylene (PTFE) available under the trademark Impra®, from Impee, in Arizona. Other suitable materials include for example: silicone rubber such as Silastic® from Dow Corning; silicone polymers; polypropylene; Impra®; Gortex®; Teflon®; and hydrophobic polyurethanes. The selection of the substrate material depends upon the mechanical and functional properties required for the implant.

Synthesis of the Triblock Polymer

The Dextran Triblock Polymer

The first step is to react dextran with epichlorohydrin, to obtain an intermediate product as shown below:

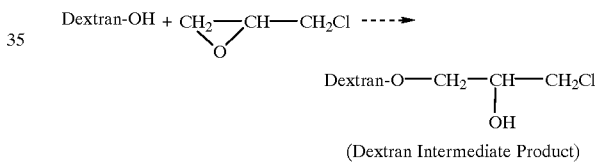

(Dextran Intermediate Product)

Next, the intermediate dextran product is reacted with an amine terminated hydrocarbon, such as, for example, 1,6-hexanediamine, as shown below:

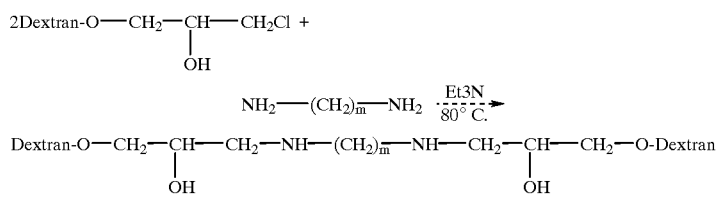

(wherein m preferably =5–18)

Though there are many hydroxyl groups on the dextran polymer chain, the reducing end, that is, the terminal hydroxyl group, is more reactive than the other hydroxyl groups. As a result, the reaction with the epichlorohydrin occurs at the reducing end of the dextran chain. Since the reaction of dextran with epichlorohydrin in the presence of sodium hydroxide is commonly used to produce a three dimensional network of crosslinked chains, sodium hydroxide was specifically excluded from the formulation.

EXAMPLE 1

A triblock polymer was prepared by adding 0.44 g (0.00005 mol) dextran, having an average MW 8,8000 from Sigma Chemical Co. to a 100 ml round-bottom flask containing 4 ml distilled water and 16 µl (0.0002 mol) 99% epichlorohydrin from Aldrich Chemical Co. The mixture was stirred at 80° C. for 4 hours. A mixture of 1 ml distilled water, 0.3 ml 98% triethylamine from Aldrich Chemical Company, and 5 mg (0.043 mmol) of 98% 1,6-hexanediamine from Aldrich Chemical Company, was added to the flask. The mixture was stirred for another 3 hours at 80° and then the dextran triblock polymer was precipitated in a large excess of acetone, washed several times with acetone and filtered. After drying overnight in a 70° C. oven, the dextran triblock polymer was ground into powder using a porcelain mortar and pestle and stored in a clean, dry bottle.

EXAMPLE 2

A triblock polymer was prepared as in Example 1 except that 10 mg (0.086 mmol) of 1,6-hexanediamine 98%, from Aldrich Chemical Company, was added instead of 5 mg.

EXAMPLE 3

A triblock polymer was prepared as in Example 1 except that 10 mg (0.05 mmol) of 1,12-diaminododecane 98%, from Aldrich Chemical Company, was added instead of 10 mg. 1,6-hexane diamine.

Synthesis of the Heparin Triblock Polymer

Heparin is a glycoprotein; its structure contains a unique pentasaccharide sequence that is responsible for its anticoagulant activity. The protein core of heparin is removed because it has no anticoagulant activity and its presence on the surface of the substrate would reduce ERF and increase the adsorption of plasma proteins.

First, an aqueous solution of crude heparin having an average MW 5,000–25,000, derived from porcine intestinal mucosa, was obtained from Sigma Chemical Co. St Louis, Mo. The crude heparin and 10.0 mg/ml sodium salt solution was passed through a 3×8 cm cation exchange column containing 200–400 mesh Dowex 50W-X8 H+ resin and washed with about 100 ml water. The pH was monitored during the ion exchange. The elutate was then mixed with 250 ml ethylene glycol dimethyl ether and cooled to –10° C. using an ice-salt bath. Partial deaminative cleavage of crude heparin was carried out by the addition of 10 ml isopentylnitrite. The reaction was quenched after 40 minutes by adjusting the pH to 8.0 with 2.0 M Tris buffer. The mixture was concentrated by vacuum distillation at 37° C., and desalted by passage through an Amicon 8400 ultrafiltration membrane having a 500 molecular weight cut-off, from Diaflo Ultrafilters Company. Next, 5 ml saturated aqueous sodium acetate solution was added to 20 ml of the mixture and poured immediately into 2 liters of stirred cold 95% ethanol. The heparin polysaccharide precipitated and was collected on a glass filter having a pore size 0.45 µm and washed with 95% ethanol. The resulting heparin polysaccharide was a mixture of polysaccharides having varying affinities for ATIII (hereinafter referred to as "mixed affinity heparin"). This mixed affinity heparin, which possesses a terminal aldehyde group on the terminal 2-5 anhydromanose unit, was joined to 1,6-hexanediamine by reductive amination in the presence of sodium cyanoborohydride.

EXAMPLE 4

A triblock polymer was prepared by adding 0.185 g of the mixed affinity heparin, (hereinafter "MA-heparin") to a 100 ml round-bottom flask containing a mixture of 4 ml distilled water, 100 mg $NaBH_3CN$. Then 80 mg (0.688 mmol) of 98% 1,6-hexanediamine from Aldrich Chemical Company was added to the flask. The mixture was stirred for 3 hours at 80° C. and then the heparin triblock polymer was precipitated in a large excess of acetone. The precipitate was washed several times with acetone and filtered on the 12.5 cm diameter filter paper. After drying overnight in a 70° C. oven, the MA-heparin triblock polymer was ground into powder using a porcelain mortar and pestle and stored in a clean, dry bottle.

Adsorption of the Triblock Polymer on Surface of Substrate

Ethylene oxide sterilized NHLBI primary reference low density polyethylene film (PE), in sheets having dimensions of 82.5 mm×27 mm×0.28 mm, from Abiomed Inc. were rinsed several times with distilled water. Aqueous solutions containing 0.32% of the triblock polymer of each of the above examples were prepared. Samples of the PE were placed in each of the solutions for 24 hours. The PE was then removed and stirred in distilled water for 1 hour. Finally, the PE was washed with distilled water several times and air-dried in a class 100 clean hood.

For controls, unmodified PE was rinsed several times with distilled water and incubated in a 0.32% aqueous solution of either dextran or heparin, in the same manner as above.

Characterization of the Dextran Triblock Polymer

The structure of the dextran triblock polymer was confirmed using four transform infra red (FTIR) spectroscopy, gel permeation chromatography and $^{13}C$-nuclear magnetic resonance spectroscopy.

FTIR Spectroscopy

FTIR transmission spectra of dextran and the dextran triblock polymer samples were obtained using the KBr pellet method on a Digilab FTS-40 FTIR spectrometer equipped with a triglycine sulfate (TGS) detector. Absorption spectra were obtained from rationing 2048 reference and sample scans which were obtained at resolution 8 $cm^{-1}$. Materials used in the preparation of the KBr pellets were ground up, dried, mixed and reground and then pressed into a pellet under reduced pressure. ATR/FTIR spectra of various PE surfaces were obtained using the same spectrometer equipped with an attenuated total reflectance (ATR) accessary available from Wilkes Scientific and a liquid nitrogen cooled mercury-cadmium-telluride (MCT) detector. A germanium crystal with dimensions of 50×20×2 mm and nominal incident angle of 45° was used as an IR internal reflection element (IRE). Spectra were obtained by co-adding 2048 interferogram scans obtained at a resolution of 8 $cm^{-1}$. All the FTIR/ATR spectra were normalized using $CH_2$ deformation vibration δ (C—H) at 1460 $cm^{-1}$ as standard to eliminate any variation in optical contact.

Figure 2:
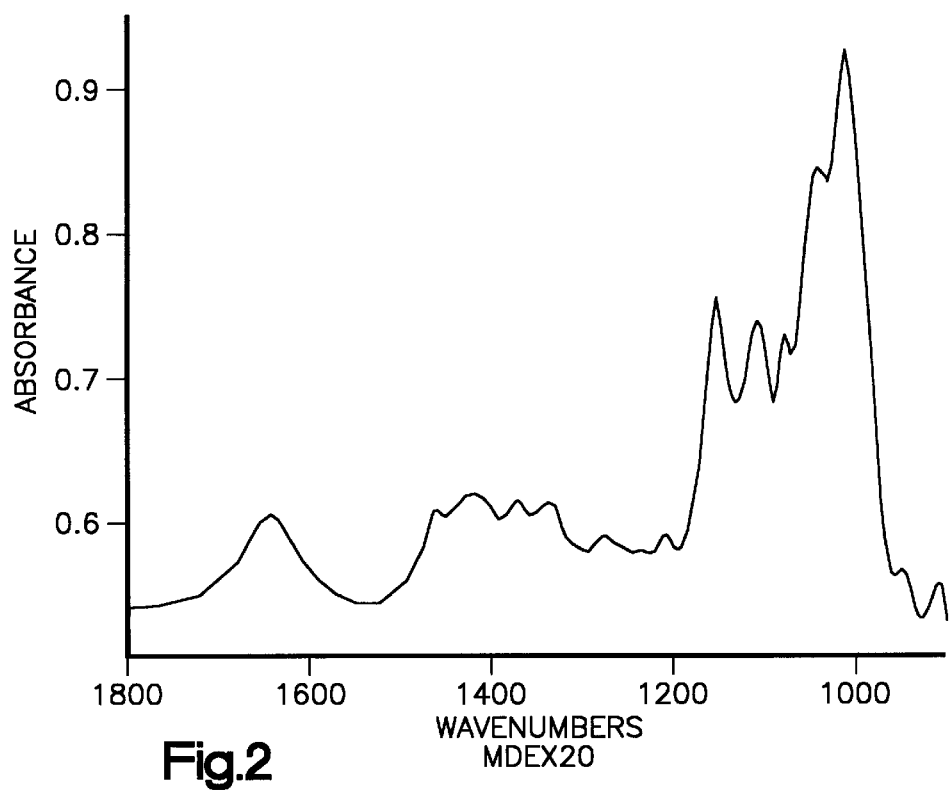
FIG. 2 is the FTIR spectrum the dextran triblock polymer.

The FTIR transmission spectrum the dextran triblock polymer is shown in FIG. 2. The spectrum shows: a strong, broad absorption band v(O—H) at ~3550 $cm^{-1}$ due to the high hydroxyl group content in dextran; stretching vibration bands vas(C—H) and vs(C—H) in $CH_2$ in the range of 2960⁻2860 $cm^{-1}$; and aliphatic bending vibration bands at 1460 $cm^{-1}$ and 1367 $cm^{-1}$. The hydroxyl in-plane bending vibration v(O—H) is located at 1410 $cm^{-1}$. Finally, the C—O—C asymmetric and symmetric stretching vibration bands are observed at 1200–1000 $cm^{-1}$.

Stretching vibrations v(N—H) were not identified above the spectral noise in the FTIR spectrum of the dextran triblock polymer because the secondary amine-functional group contributed and extremely small fractions of the long chain dextran.

Gel Permeation Chromatography

The molecular weight distribution of the free dextran and the dextran triblock polymer were determined using a 2.5×

92.5 cm Sephadex G-75 gel chromatography column. The elution solvent was a mixture of 20 mM tris+50 mM NaCl, having a pH of 7.0. The solvent flow rate was run at 2.0 ml/min. Standard linear dextrans were purchased from Sigma Chemical Company, St. Louis, Mo., and used as reference molecular weight calibration curve. The average molecular weights of these reference dextrans was 39,100, 19,600, 11,000, 8,800 and 5,000. The void volume of the column was estimated by running of a blue dextran sample (VO=175 mL). After separation, collected fractions were analyzed by the carbazole reaction for uronic acid content according to T. Bitter et al., *Anal. Biochem.*, 4:330 (1962).

Figure 3A:
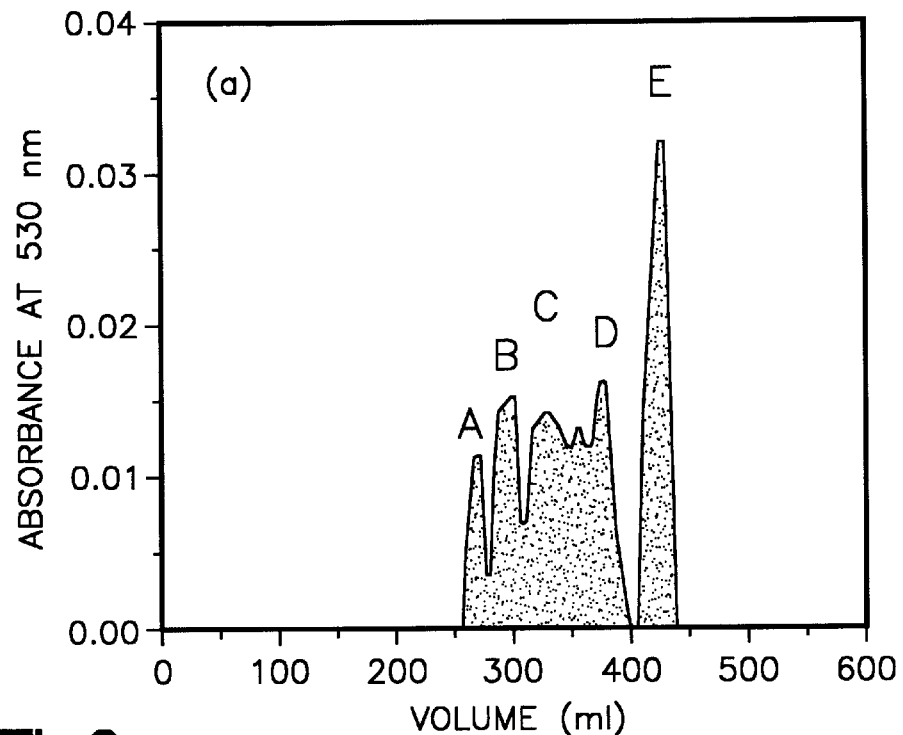
FIG. 3A is a GPC chromatogram molecular weight distribution obtained by GPC of dextran on Sephadex G-75 gel chromatography column followed by measurement of the uronic acid content. GPC elution solvent was 20 mM Tris+50 mM NaCl (pH=7.0) with flow rate of 2.0 ml/minute.
Figure 3B:
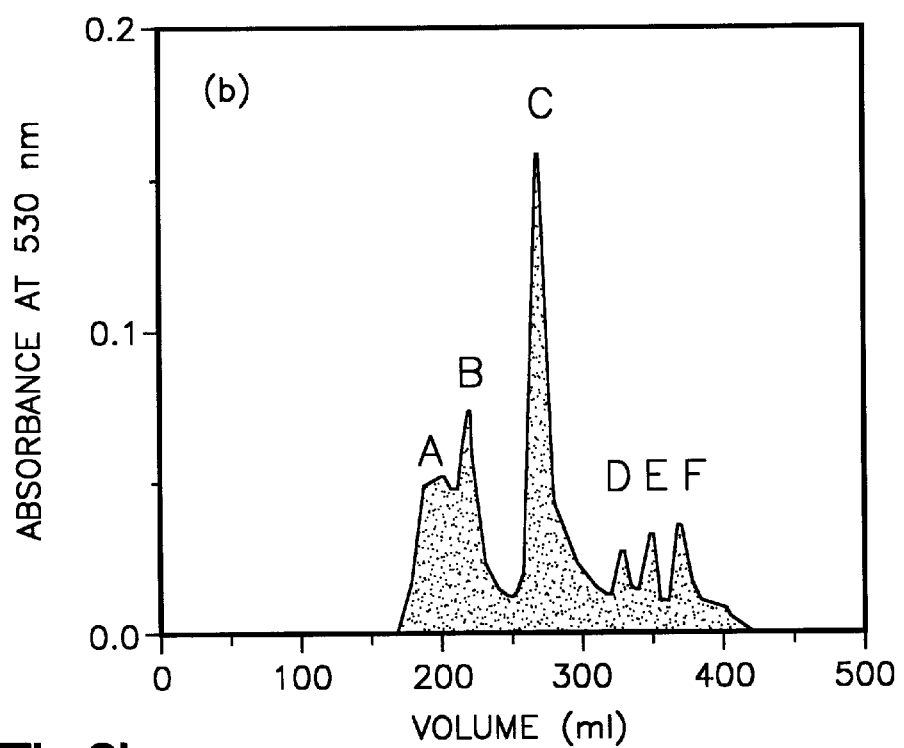
FIG. 3B is the molecular weight distribution obtained by GPC of the dextran triblock polymer on Sephadex G-75 gel chromatography column followed by measurement of the uronic acid content. GPC elution solvent was 20 mM Tris+50mM NaCl (pH=7.0) with flow rate of 2.0 ml/minute.

The Kav value was calculated and then Kav-log molecular weight linear calibration curve in which $R^2$=0.983 was obtained. The GPC chromatogram of dextran and the dextran triblock polymer are shown in FIGS. 3A and 3B. The commercial dextran used to synthesize the dextran triblock polymer, with average molecular weight of 8,800, is heterogeneous in polysaccharide chain lengths. The chromatogram of the dextran triblock polymer (FIG. 3B) shows that the molecular weight of dextran triblock polymer is much higher than that of the dextran. Kav values and the calculated molecular weights for the dextran and the dextran triblock polymer are summarized in Table I.

TABLE I

Molecular Weight Distribution of Dextran Fractions

| Samples | Kav[a] | Molecular Weight[b] (weight average) |
|---|---|---|
| Dextran fractions | | |
| A | 0.378 | 16,200 |
| B | 0.498 | 12,400 |
| C | 0.617 | 9,460 |
| D | 0.816 | 6,030 |
| E | 0.996 | 4,000 |
| Dextran Triblock Polymer fractions | | |
| A | 0.059 | 33,700 |
| B | 0.159 | 26,900 |
| C | 0.398 | 15,600 |
| D | 0.617 | 9,500 |
| E | 0.697 | 7,800 |
| F | 0.797 | 6,300 |

[a]Kav is defined as (Ve − Vo)/(Vt − Vo), where Ve = elution volume, Vo = void volume, and Vt = column volume.
[b]Molecular weights were determined by comparing the Kav values of the samples with those of dextran standards of known molecular weight.

The molecular weight of the dextran triblock polymer is approximately double that of the dextran, indicating the formation of the dextran triblock polymers. These dextran triblock polymers resulted from the using the commercial preparation in which the dextran molecules had a variety of molecular weights. The analysis did not reveal any crosslinked polymer which is consistent with the fact that the dextran triblock polymer is water soluble.

$^{13}$C-Nuclear Magnetic Resonance Spectroscopy

Proton-decoupled $^{13}$C-NMR spectra were obtained at natural abundance, with a total carbohydrate concentration of about 100 mg/2 mL of deuterium oxide. A Varian XL-200 (200 MHz) spectrometer was employed in the Fourier-transform, data processing mode. The spectra width was 6 kHz; the acquisition time, 1.4 seconds; and the pulse-width, 14 seconds. The number of transients was, in general, a function of the desired signal-to-noise ratio for each spectrum. Chemical shifts were expressed in p.p.m. relative to external tetramethylsilane, and calculated by reference to the lock signal.

Figure 4A:
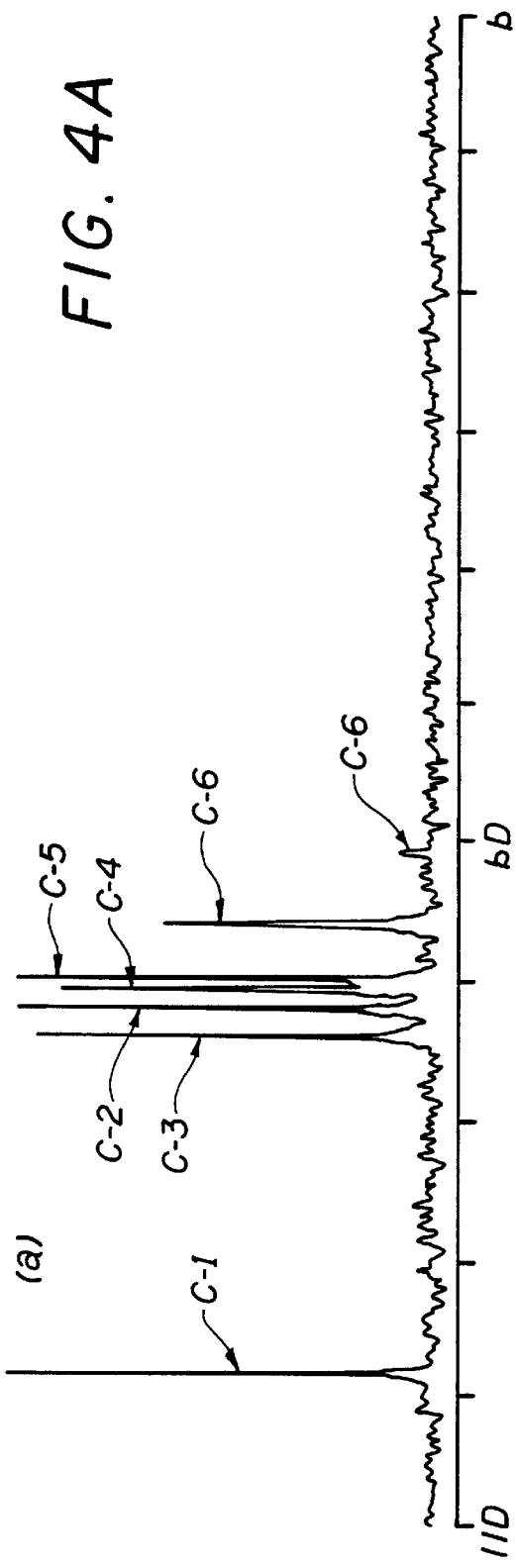
FIG. 4A is the $^{13}$C-NMR spectra of dextran.
Figure 4B:
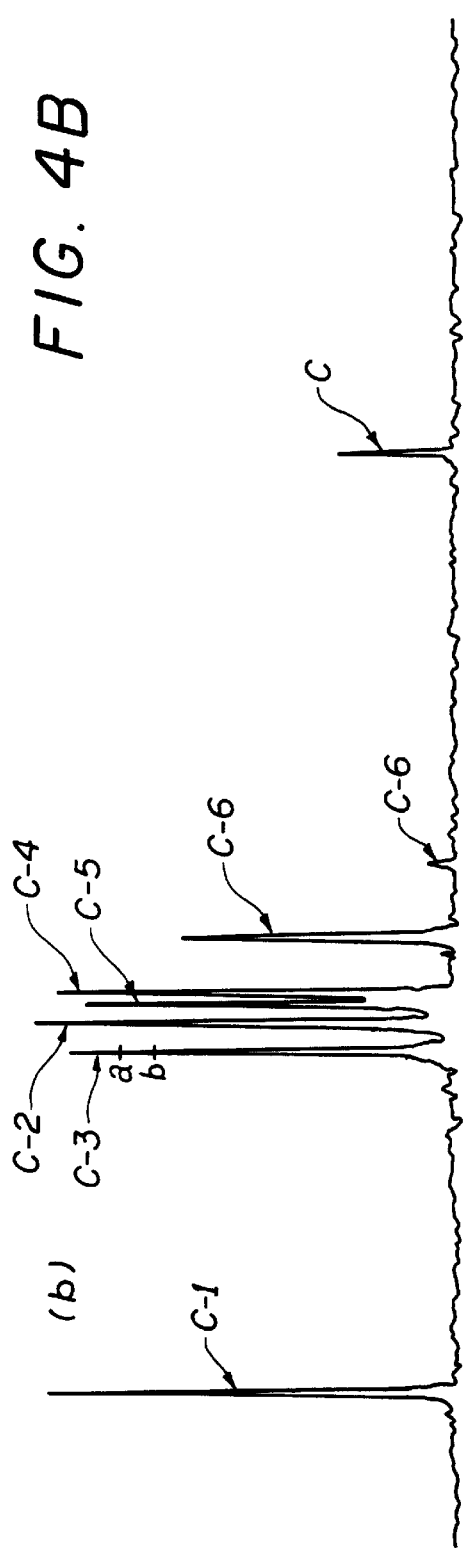
FIG. 4B is the $^{13}$C-NMR spectra of the intermediate dextran product.

The $^{13}$C-NMR spectra of the dextran, the intermediate dextran product, and the dextran triblock polymer are shown in FIGS. 4, 4B, and 4C. The $^{13}$C-NMR spectrum of the dextran shown in 4A is located mainly in three regions: The C-2,-3,-4, and -5 chemical shifts are found in the 70–75 p.p.m. region; the anomeric (C-1) carbon atom displays a downfield chemical shift in the 85 to 105 p.p.m region, mainly at 97 to 103 p.p.m., as there is only an infinitesimal proportion of reducing sugar in the polymers; and upfield chemical shifts in the 60–70 p.p.m region which are associated with bonded C-6 and unbonded C-6 atoms. The glycoside bond causes the chemical shift of the two carbon atoms involved to be displayed downfield by about 10 p.p.m. The NMR Spectra for the intermediate dextran product shown in FIG. 4B shows an upfield chemical shift at about 31 p.p.m. due to the Cl substitution. This is consistent with the measurement of chloride content in the sample obtained to titration.

The NMR Spectra for the dextran triblock polymer is shown in FIG. 4C. As a result of the reaction with the amine terminated hydrocarbon, the chemical shift seen in the intermediate dextran product at about 31 p.p.m. was not present. However, the chemical shifts were observed at 55 p.p.m. for the c-carbon, at 53 p.p.m. for the d-carbon, and 24.04 p.p.m. assigned to e and f carbons.

In contrast to $^1$H-NMR spectra, the peak area for $^{13}$C-NMR spectra does not necessarily reflect the population of atoms present. However, for carbohydrates, including polysaccharides, it has been shown that peak height is, in general, proportional to the number of carbon species present.

Figure 5:
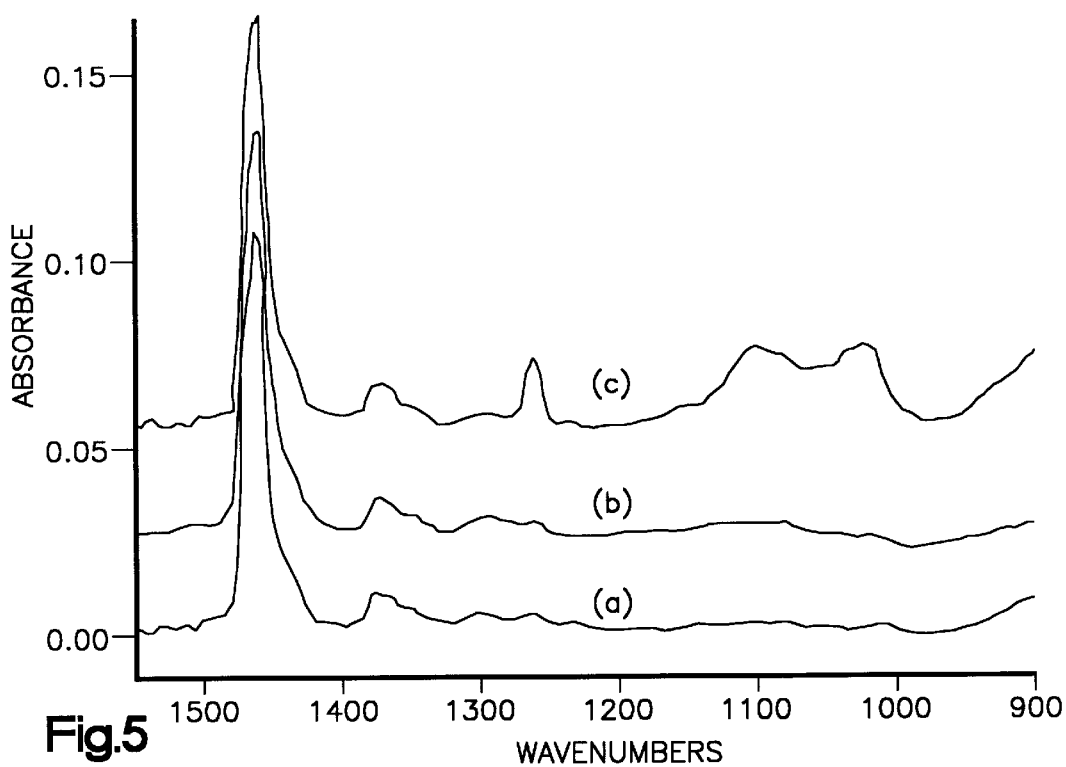
FIG. 5 is the FTIR/ Attenuated Total Reflectance (ATR) spectra (1550–900 cm$^{-1}$ region) of: (a) unmodified PE; (b) PE exposed to dextran solution; (c) dextran triblock polymer adsorbed on PE.

Hydrophobic Interaction of the Dextran Triblock Polymer with the surface of the PE FIG. 5 shows the ATR/FTIR spectra of unmodified PE, PE exposed to the dextran solution and dextran triblock polymer adsorbed PE. The dextran triblock polymer adsorbed PE had VC—O—C absorption bands at 1200–1000 cm$^{-1}$. The PE exposed to the dextran solution shows the same spectra as the unmodified PE, which establishes that the dextran does not bind to the surface of the PE.

Figure 5A:
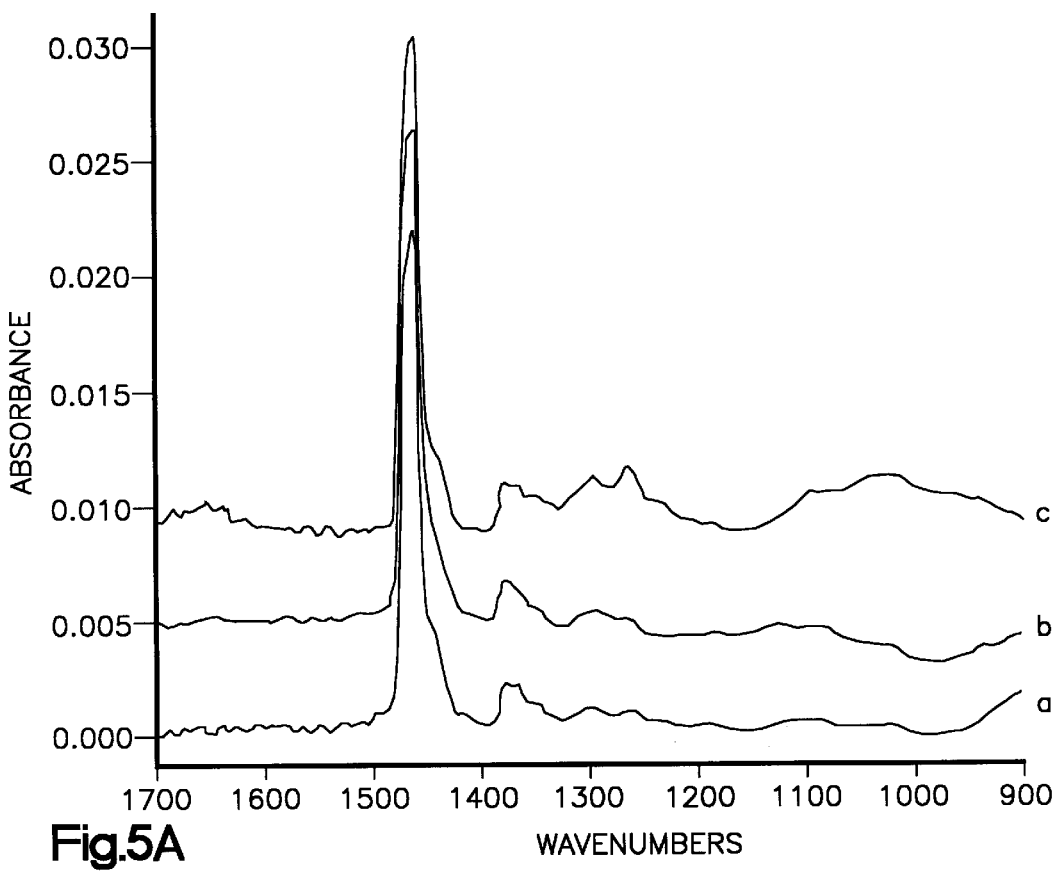
FIG. 5A is the FTIR/ Attenuated Total Reflectance (ATR) spectra (1700–900 cm$^{-1}$ region) of: (a) unmodified PE; (b) PE exposed to heparin solution; (c) heparin triblock polymer adsorbed on PE.

FIG. 5A shows the ATR/FTIR spectra of unmodified PE, PE exposed to the heparin solution and heparin triblock polymer adsorbed PE. As shown in FIG. 5A, spectra c, the heparin triblock polymer adsorbed PE had VC—O—C absorption bands at 1200–1000 cm$^{-1}$. The PE exposed to the heparin solution, spectra b, shows the same spectra as the unmodified PE, spectra a, which establishes that the heparin does not bind to the surface of the PE.

Figure 6:
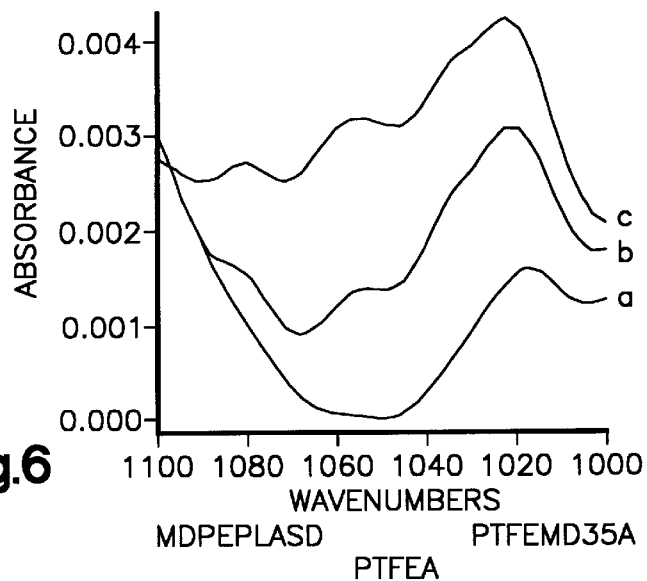
FIG. 6 is the FTIR/ Attenuated Total Reflectance (ATR) spectra (1100–1000 cm$^{-1}$ region) of: (a) unmodified Impra®; (b) a dextran triblock polymer adsorbed on Impra and (c) dextran triblock polymer adsorbed on PE (for comparison).

FIG. 6 shows the ART/FTIR spectra of unmodified Impra®, and dextran triblock polymer adsorbed Impra®. The dextran triblock polymer adsorbed Impra® had vc-o-c adsorption bands at 1080 cm$^{-1}$ and 1056 cm$^{-1}$ (see spectr b) which are characteristic of the dextran; compare to spectra c the spectra for dextran triblock polymer adsorbed PE. The unmodified Impra® sample lacks such bands.

Water Contact Angle Measurement

Advancing water contact angle ($\theta_A$) was measured by the sessile-drop method using a Rame-Hart goniometer. The water contact angle measurment is a surface sensitive assay ofthe top 5–10 angstroms of the surface of a material. The presence of hydrophillic molecule on the surface should reduce the water contact angle. The advancing water contact angle θ a H$_2$O were measured by placing a 2 µl water drop onto the PE surface using a microsyringe attachment. A second 2 µL drop was added to the first drop and the new contact angle was measured. The process was repeated three additional times and the results represented the measurement of θ a $H_2O$. Measurement of water contact angle was repeated four times for each sample. All the contact angle measurements were performed at room temperature and about 50% relative humidity.

The unmodified PE surface is hydrophobic and has water contact angle of about 90°. The water contact angle of the dextran triblock polymer adsorbed on PE is about 75° and shows very small contact angle hysteresis. This decrease is the water contact angle confirms the presence of the hydrophillic dextran molecule on the substrate.

ESCA Analysis

ESCA analysis is a surface analysis of the top 6 nm of the material. Surface analysis of the unmodified PE and the dextran triblock polymer adsorbed PE was performed using a Perkin Elmer PHI-5400 ESCA system with a 400 W monochromatized magnesium X-ray source at 44.74 pass energy and 45° take off angle. The results are shown in Table II.

About 1.3% oxygen, 98.7% carbon and 0% nitrogen were detected on the surface of the unmodified PE control. All the dextran triblock polymer adsorbed PE samples showed a substantial increase in the percent of oxygen and nitrogen present on the surface of the samples. The increased amount of the oxygen on the surface of the dextran triblock polymer adsorbed PE, confirms the presence of the dextran segment of the triblock polymer. The presence of the nitrogen confirms the presence of the amine groups present in the hydrocarbon chain of the triblock polymer. No chloride content was detected on the dextran triblock polymer adsorbed PE. The PE exposed to dextran solution showed results similar to the unmodified PE control.

TABLE II

Atomic Concentration of Dextran Adsorbed PE

| Sample | Atomic Concentration (%) | | |
|---|---|---|---|
| | O1s | N1s | C1S |
| Unmodified PE | 1.3 | 0 | 98.7 |
| Example 3 | 17.9 | 1.8 | 80.3 |
| Example 2 | 21.9 | 1.1 | 77.0 |
| Example 1 | 9.4 | 0.9 | 89.7 |

Atomic concentration was determined by ESCA spectrometer operated in survey scan mode. Estimated error for ESCA analysis is +10%.

The ESCA, ATR/FTIR and water contact angle results confirm the presence of the dextran triblock polymer on the PE surface. Since the PE exposed to the dextran solution does not show the presence of dextran, the adsorption of the triblock polymer results from the hydrophobic interaction between the PE surface and the hydrocarbon chain in the dextran triblock polymer.

Protein Resistance of Triblock Polymer Adsorbed PE

Albumin is the most abundant protein present in blood plasma constituting about 50% of the total protein in plasma. Albumin is often a major constituent of the protein layer that is deposited on polymeric implants. Accordingly, the triblock polymer coated substrates were evaluated for resistance to albumin deposition.

Samples of the unmodified PE, unmodified Impra®, the dextran triblock polymer adsorbed PE and the dextran triblock polymer adsorbed Impra® were rinsed in distilled water and put into 5% bovine albumin solution from Sigma Chemical Company for 24 hours. The bovine albumin solution, which had a pH of about 7, was sterile filtered, and contained 0.70% NaCl. Then the samples were stirred in distilled water for 2 hours, washed several times with distilled water, and air-dried in a hood for 24 hours at room temperature.

Figure 7:
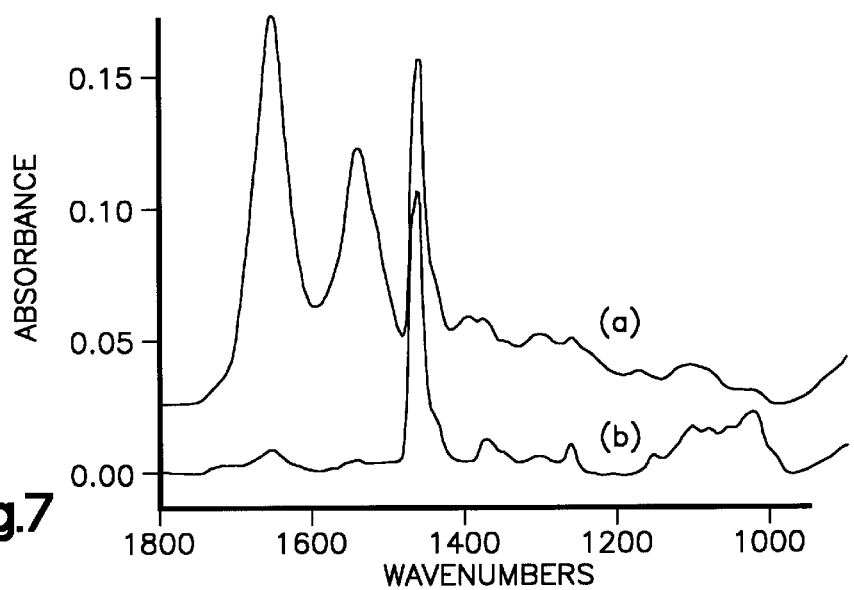
FIG. 7 is a FTIR/ATR spectra (1800–900 cm$^{-1}$ region) of unmodified PE exposed to: (a) 5% albumin solution for 24 hours; and (b) dextran triblock polymer adsorbed on PE exposed to 5% albumin solution for 24 hours.

FIG. 7 shows normalized ATR/FTIR spectra of unmodified PE (spectra b) and the dextran triblock polymer adsorbed PE (spectra a) after incubation in the 5% albumin solution. Spectra were normalized to the (C—H) band at 1460 $cm^{-1}$ in PE so that the absorbencies are directly comparable. The relative amount of albumin adsorbed on the surface of the PE was calculated from the amide I absorption bands at 1650 $cm^{-1}$ with baseline correction and normalization to polyethylene deformation vibration (in-plane) at 1460 $cm^{-1}$.

The unmodified PE shows strong amide I and amide II absorption bands at 1650 and 1550 $cm^{-1}$, respectively, which are characteristic of the albumin. The spectrum shows that the albumin strongly absorbed onto the unmodified PE surface. However, the spectra of the dextran triblock polymer adsorbed PE display weak amide I and amide II absorption bands as compared to unmodified PE. Only about 8.5%+3% albumin was adsorbed on the dextran triblock polymer adsorbed PE surface compared with the unmodified PE.

Figure 8:
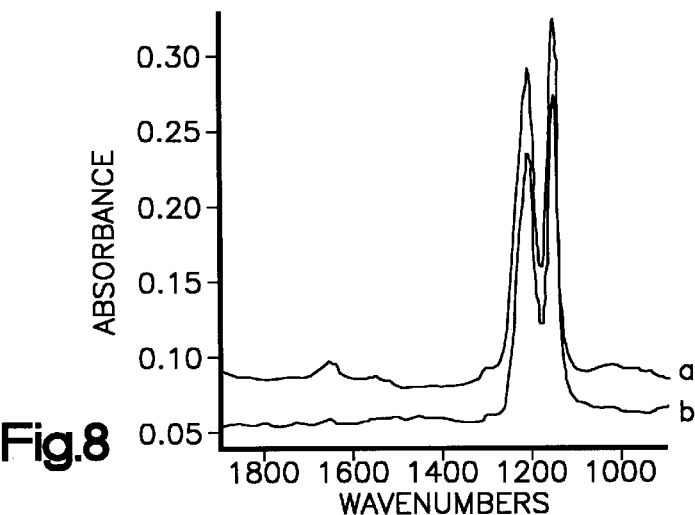
FIG. 8 is a FTIR/ATR spectra (1800–900 cm$^{-1}$ region) of unmodified Impra® exposed to 5% albumin solution for 24 hours (a), and dextran triblock polymer adsorbed on Impra® exposed to 5% albumin solution for 24 hours(b).

FIG. 8 shows normalized ATR/FTIR spectra of unmodified Impra® and the dextran triblock polymer adsorbed Impra® after incubation in the 5% albumin solution. Spectra were normalized to the (C—H) band at 1150 or 1225 $cm^{-1}$ in the Impra® so that the absorbencies are directly comparable. The relative amount of albumin adsorbed on the surface of the Impra® was calculated from the amide I absorption bands at 1650 $cm^{-1}$ with baseline correction and normalization to Impra® deformation vibration.

The unmodified Impra® shows strong amide I and amide II absorption bands at 1650 and 1550 $cm^{-1}$, respectively, which are characteristic of the albumin. Thus, the spectrum shows that the albumin absorbed onto the unmodified Impra® surface. However, the spectra of the dextran triblock polymer adsorbed Impra® lack the amide I and amide II absorption bands.

Samples of the unmodified PE and the mixed affinity heparin triblock polymer adsorbed PE, were exposed to fresh human blood plasma for 1 hours. The the samples were stirred in distilled water for about 1 hour, washed several times with distilled water, and air dried in a hood for about 1 hour at room temperature.

Figure 10:
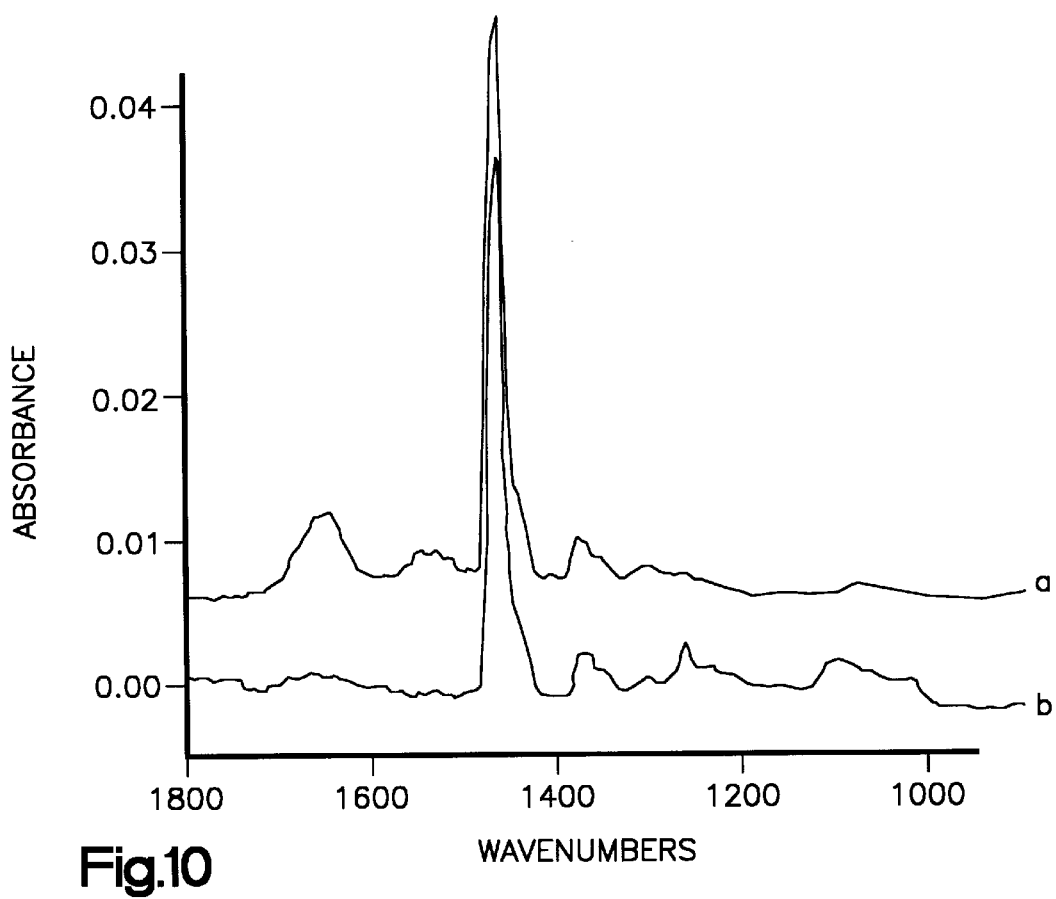
FIG. 10 is a FTIR/ATR spectra (1800–900 cm$^{-1}$ region) of: (a) unmodified PE exposed to human plasma; and (b) heparin triblock polymer adsorbed PE exposed to human plasma.

FIG. 10 show normalized ATR/FTTR spectra of unmodified PE (spectra a) and the heparin triblock adsorped PE (spectra b) after incubation in the plasma. Spectra were normalized as for FIG. 7. The spectra of the heparin triblock polymer adsorbed PE lacks the characteristic amide I and amide II bands characteristic of albumin, demonstrating that the heparin triblock adsorbed PE resists plasma protein deposition.

UV Spectroscopy

Figure 9:
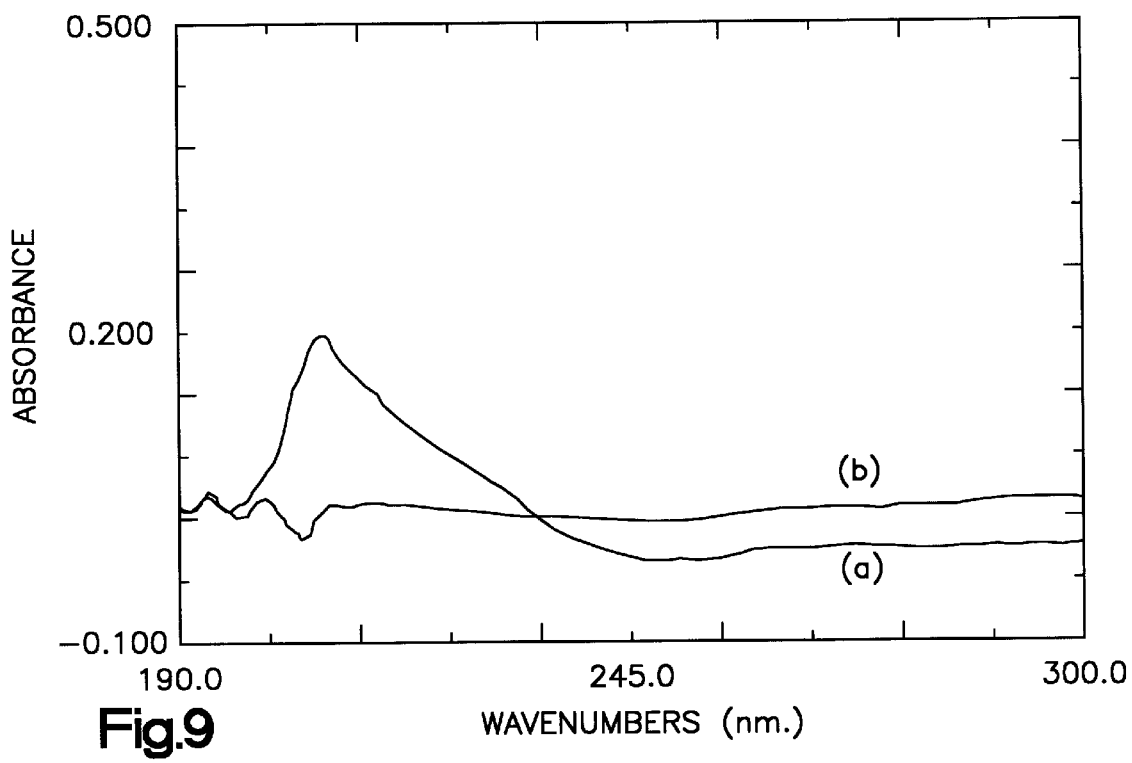
FIG. 9 is a UV spectra (190–300 nm region) of: (a) unmodified PE exposed to 5% albumin solution for 24 hours; and (b) dextran triblock polymer adsorbed PE exposed to 5% albumin solution for 24 hours.

UV spectra of unmodified PE and the triblock polymer adsorbed PE, which were exposed to albumin, were obtained using a UV-VIS Scanning Spectrophotometer system designated as UV-2101PC from Shimadzu Corporation. Sample were fixed on the sample side of the film holder model P/N204-58909, from Shimadzu Corporation. The unmodified PE was fixed on the reference side. FIG. 9 is the UV spectrum of unmodified PE; it shows a strong absorption band at 208 nm. In contrast, as shown in FIG. 9, spectra b, the dextran triblock polymer adsorbed PE does not show such band; the triblock polymer pre-adsorbed PE did not adsorb the albumin.

Rotating Disc Experiments

To determine the stability of the triblock polymers on the PE surface under high interfacial shear conditions, samples of the triblock polymer adsorbed PE were cut into 17 mm diameter discs and mounted on the disc of spindle assembly of a Model Afasr Analytical Rotator from Pine Instrument Co. The discs were stirred for 1 hour at 2000 rpm in solutions of either PBS buffer, 5% sodium dodecylsulfate solution (SDS), 5% bovine albumin solution, or fresh human plasma. The samples were then washed several times with distilled water. The shear stress under these conditions was calculated as about 206 dynes/cm² at the edge of the sample.

The shear stress was determined by:

$$\tau = 0.800 \; \eta r \; (\omega^3/\nu)^{0.5}$$

where $\tau$ is the magnitude of shear stress at the disk surface (dynes/cm²), $\eta$ is the absolute viscosity (0.011 poise), and r is the radial distance from the center of the disk (8 cm), $\omega$ is the angular velocity (209.4 rads/sec), and v is the knematic viscosity (0.0107 stokes). Under the conditions of 5% albumin solution or human plasma, this produces a protein flux at the surface of 0.52–0.56 $\mu$g/mm² sec as calculated from:

$$j = 0.62 \; D^{2/3} \; \nu^{1/6} \; \omega^{1/2} \; C_\infty$$

where j is the mass flux, D is the diffusivity ($4.04 \times 10^{-7}$ cm²/sec), $C_\infty$ is the bulk concentration (5 g/dL), v and $\omega$ are as above.

All spectra were normalized to the 1460 cm⁻¹ band of unmodified PE, so that the spectra may be directly compared. The absorbance scale for FIGS. 5, 9, and 11 are identical.

Figure 11:
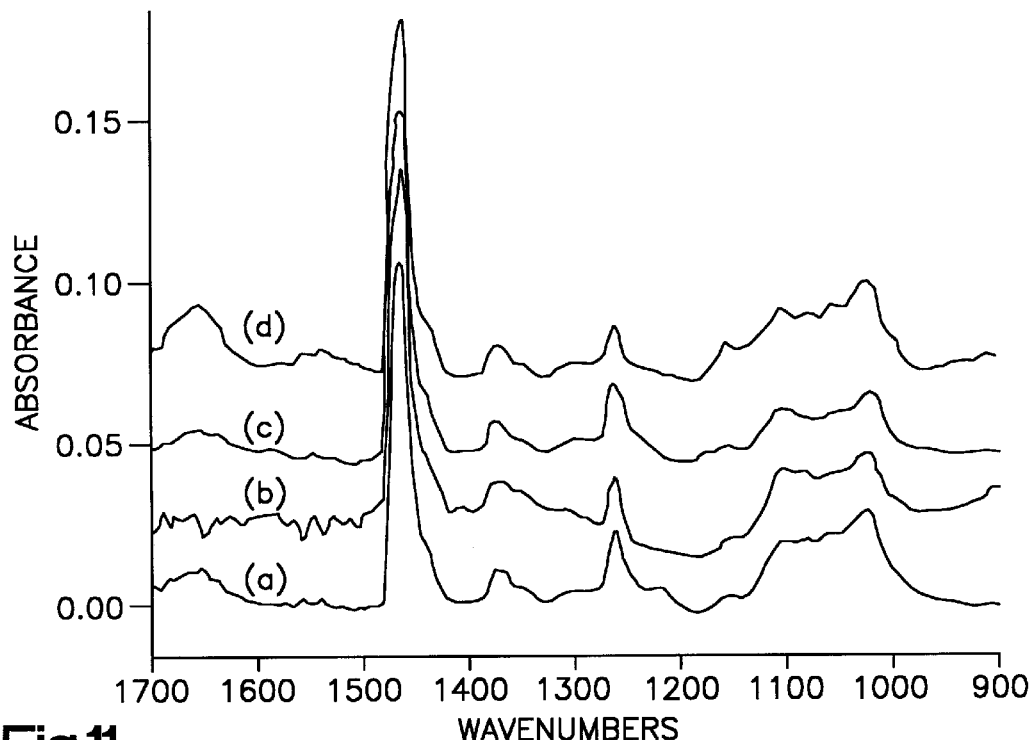
FIG. 11 is a FTIR/ATR spectra (1700–900 cm$^{-1}$ region) of dextran triblock polymer adsorbed PE exposed to: (a) PBS buffer solution, (b) 5% SDS solution, (c) 5% albumin solution, (d) human plasma.

FIG. 11 shows ATR/FTIR spectra of the dextran triblock polymer adsorbed PE after rotating in the solutions. Spectra "a" is the spectra of the sample that rotated in PBS buffer solution, "b" is the spectra of the sample that rotated in 5% SDS solution, "c" is the spectra of the sample that rotated in 5% albumin solution, and "d" is the spectra of the sample that rotated in human plasma solution. All the samples show the absorption bands of dextran at 1200–1000 cm⁻¹; the triblock polymer remained bound to the PE despite the shear conditions. Further, as evidenced by spectra c and d, which revealed weak absorption bands of amide I and amide the dextran triblock polymer adsorbed PE does not significantly adsorb albumin or other plasma proteins.

Figure 12:
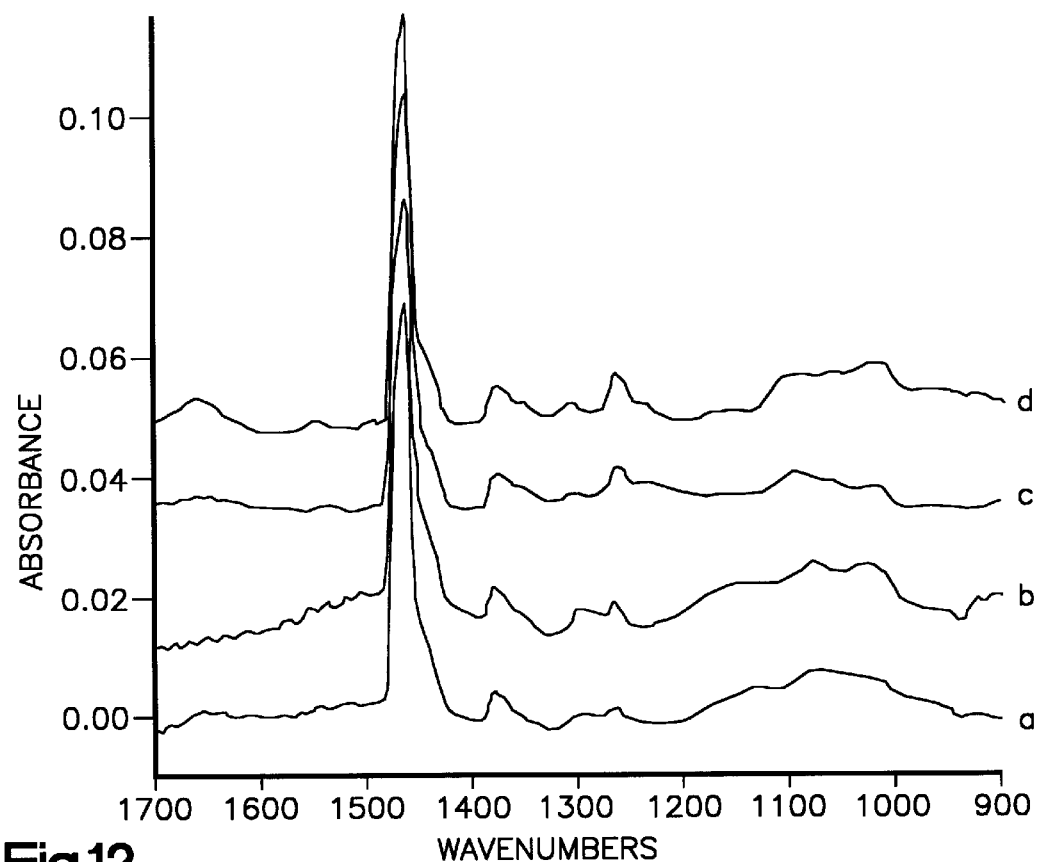
FIG. 12 is a FTIR/ATR spectra (1700–900 cm$^{-1}$ region) of heparin triblock polymer adsorbed PE exposed to: (a) PBS buffer solution, (b) 5% SDS solution, (c) 5% albumin solution, (d) human plasma.

FIG. 12 shows ATR/FTIR spectra of the heparin triblock polymer adsorbed PE surfaces after rotating in the solutions. Spectra "a" is the spectra of the sample that rotated in PBS buffer solution, "b" is the spectra of the sample that rotated in 5% SDS solution, "c" is the spectra of the sample that rotated in 5% albumin solution, and "d" is the spectra of the sample that rotated in human plasma solution. All the samples show the absorption bands characteristic of the heparin at 1250 cm⁻¹ and at 1120–950 cm⁻¹ the triblock polymer remained bound to the PE despite the shear conditions. Further, as evidenced by spectra c and d, which revealed weak absorption bands of amide I and amide II, the heparin triblock polymer adsorbed PE does not significantly adsorb albumin or other plasma proteins.

The results establish that the triblock polymers have been formed, coated and that they tightly bind to the substrates. Indeed, the triblock polymers remained bound to the PE after being subjected to a shear rate of 206 dynes/cm². This indicates that there is a strong binding force between the hydrophobic hydrocarbon segment of the triblock polymer and substrate surface, to provide a strong, stable interface between the substrate and the triblock polymer. Moreover, the triblock polymer provides the substrate with resistance to plasma protein binding, including resistance to albumin binding.

Although this invention has been shown and described as a triblock polymer having two polysaccharide segments and one hydrocarbon chain segment, various adaptations and modifications can be made, such as a diblock polymer having one polysaccharide segment and one hydrocarbon chain segment, without departing from the scope of the invention as defined in the appended claims.

We claim:

1. A method for reducing the thrombogenicity of a hydrophobic substrate, comprising the following steps:
   a. providing a water soluble block polymer comprising at least one hydrophobic block comprising a hydrocarbon chain having from 5 carbons to 18 carbons and at least one polysaccharide block having a weight average molecular weight of at least 4,000, said hydrophobic block being attached to the polysaccharide block; and
   b. attaching the block polymer to the surface of the substrate through a hydrophobic interaction between the surface of the substrate and the hydrocarbon chain to provide a hydrophobic substrate with reduced thrombogenicity;

wherein the hydrophobic interaction is of sufficient strength to withstand a shear stress of 206 dynes/cm²; and wherein said block polymer is not attached to the surface of the substrate through covalent bonds.

2. The method of claim 1, wherein the hydrophobic hydrocarbon chain has from 5 to 13 carbons.

3. The method of claim 1, wherein the substrate is comprised of polyethylene.

4. The method of claim 1 wherein the substrate is comprised of polytetrafluoroethylene.

5. The method of claim 1, wherein the hydrophobic hydrocarbon is derived from 1,6-hexanediamine.

6. The method of claim 1, wherein the hydrophobic hydrocarbon is derived from 1,12-diaminododecane.

7. The method of claim 1, wherein the polysaccharide is dextran.

8. The method of claim 1, wherein the polysaccharide is heparin.

9. The method of claim 1, wherein the polysaccharide is dermatan sulfate.

10. The method of claim 1, wherein the polysaccharide is dextran sulfate.

11. The method of claim 1, wherein the polysaccharide is dextran, and the hydrocarbon is derived from 1,6-hexanediamine.

12. The method of claim 1, wherein the polysaccharide is dextran, and the hydrocarbon is derived from 1,12-diaminododecane.

13. The method of claim 1, wherein the polysaccharide is heparin, and the hydrocarbon is 1,6-hexanediamine.

14. The method of claim 1, wherein the polysaccharide is heparin, and the hydrocarbon is 1,12-diaminododecane.

15. The method of claim 1 wherein the block polymer is attached to the surface of the substrate in step (b) by a process comprising the steps of:
   a. contacting the surface of the substrate with an aqueous solution of the block polymer for a time sufficient for the block polymer to form a hydrophobic interaction with the surface of the substrate; and b. rinsing the surface of the substrate to remove unattached block polymer.

16. The method of claim 1 wherein the process of attaching the block polymer to the surface of the substrate in step (b) consists essentially of:
   a. contacting the surface of the substrate with an aqueous solution of the block polymer for a time sufficient for the block polymer to form a hydrophobic interaction with the surface of the substrate; and
   b. rinsing the surface of the substrate to remove unattached block polymer.

17. A substrate having a block polymer attached to a hydrophobic surface thereof, said block polymer comprising: at least one hydrophobic block comprising a hydrocarbon chain having from 5 carbons to 18 carbons; and at least one polysaccharide having a weight average molecular weight of at least 4,000, wherein said polysaccharide block is attached to said hydrophobic block, wherein the block polymer is water soluble, wherein the block polymer is attached to the surface of the substrate through a hydrophobic interaction of sufficient strength to withstand a shear stress of 206 dynes/cm$^2$; and
   wherein said block polymer is not attached to the surface of the substrate through covalent bonds.

18. The substrate of claim 17, wherein the hydrophobic hydrocarbon chain has from 5 to 13 carbons.

19. The substrate of claim 17, wherein the hydrophobic block comprises a hydrocarbon chain having 6 carbons.

20. The substrate of claim 17, wherein the hydrophobic block comprises a hydrocarbon chain having 12 carbons.

21. The substrate of claim 17, wherein the polysaccharide is dextran.

22. The substrate of claim 17, wherein the polysaccharide is heparin.

23. The substrate of claim 17, wherein the polysaccharide is dermatan sulfate.

24. The substrate of claim 17, wherein the polysaccharide is dextran sulfate.

25. The substrate of claim 17, wherein the polysaccharide is dextran, and the hydrocarbon chain has six carbons.

26. The substrate of claim 17, wherein the polysaccharide is dextran, and the hydrocarbon chain has 12 carbons.

27. The substrate of claim 17, wherein the polysaccharide is heparin, and the hydrocarbon chain has 6 carbons.

28. The substrate of claim 17, wherein the polysaccharide is heparin, and the hydrocarbon chain has 12 carbons.

29. A substrate having a polymer attached to a hydrophobic surface thereof, said polymer comprising at least one hydrocarbon chain and at least one polysaccharide, said hydrocarbon chain having at least 5 carbons and said polysaccharide having a weight average molecular weight of at least 4,000;
   wherein the hydrocarbon chain attaches said polymer to the hydrophobic substrate through a hydrophobic interaction of sufficient strength to withstand a shear stress of 206 dynes/cm$^2$;
   wherein said block polymer is not attached to the surface of the substrate through covalent bonds; and
   wherein the polymer is water soluble.

30. The invention of claim 19, wherein the substrate is comprised of polyethylene.

31. The invention of claim 19, wherein the substrate is comprised of polytetrafluoroethylene.

* * * * *